United States Patent
Rapoza

(10) Patent No.: US 9,744,058 B2
(45) Date of Patent: Aug. 29, 2017

(54) METHODS OF TREATMENT DIRECTED TO NEOINTIMAL PROLIFERATION GENERATED BY ENDOTHELIAL SHEAR STRESS PATTERNS FROM DRUG-ELUTING BIORESORBABLE VASCULAR SCAFFOLD IMPLANTATION

(71) Applicant: Abbott Cardiovascular Systems Inc., Santa Clara, CA (US)

(72) Inventor: Richard Rapoza, San Francisco, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 0 days.

(21) Appl. No.: 13/999,356

(22) Filed: Feb. 14, 2014

(65) Prior Publication Data

US 2014/0228932 A1    Aug. 14, 2014

Related U.S. Application Data

(60) Provisional application No. 61/765,001, filed on Feb. 14, 2013.

(51) Int. Cl.
*A61F 2/82*    (2013.01)

(52) U.S. Cl.
CPC ..................... *A61F 2/82* (2013.01)

(58) Field of Classification Search
None
See application file for complete search history.

(56) References Cited

U.S. PATENT DOCUMENTS

| | | | |
|---|---|---|---|
| 2008/0195189 A1* | 8/2008 | Asgari | A61L 31/022 623/1.2 |
| 2008/0275537 A1 | 11/2008 | Limon | |
| 2010/0019833 A1 | 1/2010 | Zang et al. | |

OTHER PUBLICATIONS

Gijsen et al., Differences in Neointimal Thickness Between the Adluminal and the Abluminal Sides of Malapposed and Side-Branch Struts in a Polylactide Bioresorbably Scaffold, Aug. 2012, JACC: Cardiovascular Interventions, vol. 5 No. 4, pp. 428-434.*
LaDisa et al., Stent design properties and deployment ration influence indexes of wall shear stress: a three-dimensional computational fluid dynamics investigation within a noraml artery, Feb. 6, 2004, Journal of Applied Physiology, vol. 97, pp. 424-430.*
"ABSORB Cohort B Trial: Two Year Clinical and Angiographic Results of the ABSORB Bioresorbable Everolimus Eluting Vascular Scaffold", JACC vol. 58 Suppl. B66, TCT Abstracts 2 pgs. (2011).
Brugaletta et al., "Circumferential evaluation of the neointima by optical coherence tomography after ABSORB bioresorbable vascular scaffold implantation: Can the scaffold cap the plaque?", Atherosclerosis 221 pp. 106-112 (2012).

(Continued)

*Primary Examiner* — Thomas J Sweet
*Assistant Examiner* — Wade P Schutte
(74) *Attorney, Agent, or Firm* — Squire Patton Boggs (US) LLP

(57) ABSTRACT

Treatments of coronary heart disease including the effect of endothelial shear stress (ESS) on neointimal formation following a bioresorbable vascular scaffold implantation are disclosed.

7 Claims, 7 Drawing Sheets
(5 of 7 Drawing Sheet(s) Filed in Color)

(56) References Cited

OTHER PUBLICATIONS

Dudek et al., "Four-year clinical follow-up of the ABSORB everolimus-eluting bioresorbable vascular scaffold in patients with de novo coronary artery disease: the ABSORB trial", Eurointervention 7, pp. 1060-1061 (2012).

Duraiswamy et al., "Comparison of Near-wall Hemodynamic Parameters in Stented Artery Models", J. Biomech. Eng. 131(6), 22 pgs. (2009).

Evaluation of the Second Generation of a Bioresorbable Everolimus Drug-Eluting Vascular Scaffold for Treatment of De Novo Coronary Artery Stenosis: Six-Month Clinical and Imaging Outcomes, Circulation 122, pp. 2301-2312 (2010).

Gijsen et al., "Usefulness of Shear Stress Pattern in Predicting Neointima Distribution in Sirolimus-Eluting Stents in Coronary Arteries", Am. J. Cardiol. 92 pp. 1325-1328 (2003).

Gomez-Lara et al., "A Comparison of the Conformability of Everolimus-Eluting Bioresorbable Vascular Scaffolds to Metal Platform Coronary Stents", JACC Cardiovascular Interventions vol. 3, No. 11, pp. 1190-1198 (2010).

Gomez-Lara et al., "Serial Analysis of the Malapposed and Uncovered Struts of the New Generation of Everolimus-Eluting Bioresorbable Scaffold with Optical Coherence Tomography", JACC Cardiovascular Interventions vol. 4, No. 9, pp. 992-1001 (2011).

Gutiérrez-Chico et al., "Spatial Distribution and Temporal Evolution of Scattering Centers by Optical Coherence Tomography in the Poly(L-Lactide) Backbone of a Bioresorbable Vascular Scaffold", Circulation J. vol. 76, 9 pgs. (2012).

Ormiston et al., "A bioabsorbable everolimus-eluting coronary stent system for patients with single de-novo coronary artery lesions (ABSORB): a prospective open-label trial ", www.thelacent.com vol. 371, pp. 899-907 (2008).

Ormiston et al., "First Serial Assessment at 6 Month and 2 Years of the Second Generation of Absorb Everolimus-Eluting Bioresorbable Vascular Scaffold: A Multi-Imaging Modality Study", Circ. Cardiovasc, Interv. 5, pp. 620-632 (2012).

Papafaklis et al., "The Effect of Shear Stress on Neointimal Response Following Sirolimus-and Paclitaxel-Eluting Stent Implantation Compared with Bare-Metal Stents in Humans", JACC: Cardiovascular Interventions vol. 3, No. 11 pp. 1181-1189 (2010).

Serruys et al., "From metallic cages to transient bioresorbable scaffolds: change in paradigm of coronary revascularization in the upcoming decade?", European Heart J. 33, pp. 16-25 (2012).

Stone et al., "In Vivo Assessment of the Risk Profile of Evolving Individual Coronary Plaques: A Step Closer", Circulation 124, pp. 763-765 (2011).

Yazdami et al., "In vitro and in vivo characterization of biodegradable polymer-based drug-eluting stent", Eurointervention 7, pp. 835-843 (2011).

* cited by examiner

METHODS OF TREATMENT DIRECTED TO NEOINTIMAL PROLIFERATION GENERATED BY ENDOTHELIAL SHEAR STRESS PATTERNS FROM DRUG-ELUTING BIORESORBABLE VASCULAR SCAFFOLD IMPLANTATION

This application claims the benefit of U.S. Application Ser. No. 61/765,001 filed Feb. 14, 2013 and is incorporated by reference herein for all purposes.

BACKGROUND OF THE INVENTION

Field of the Invention

This invention relates to methods of treatment of coronary and peripheral artery disease of human patients with bioresorbable polymer scaffolds, in particular, treatments in which shear stress of blood flow past such scaffolds effects neointimal formation.

Description of the State of the Art

This invention relates generally to methods of treatment with radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a section or segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffold gets its name because it physically holds open and, if desired, expands the wall of a passageway in a patient. Typically, stents are capable of being compressed or crimped onto a catheter from a fabricated diameter to a reduced diameter so that they can be delivered to and deployed at a treatment site.

Delivery includes inserting the stent through small lumens using a catheter and transporting it to the treatment site. Deployment includes expanding the stent to a larger target diameter once it is at the desired location. During deployment the stent makes contact with the vessel wall as it expands and expands the vessel to the larger target diameter. Mechanical intervention with stents has reduced the rate of restenosis as compared to balloon angioplasty.

Stents are used not only for mechanical intervention but also as vehicles for providing biological therapy. Biological therapy uses medicated stents to locally administer a therapeutic substance to a blood vessel. The therapeutic substance can also mitigate an adverse biological response to the presence of the stent. For example, the stent can deliver an antiproliferative agent to the vessel to prevent or mitigate neointimal proliferation caused by the stent implantation which could result in narrowing of the vessel at the site of the stent implantation. Additionally or alternatively, an anti-inflammatory agent can be delivered to reduce inflammation to the vessel wall due to the stent implantation.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must have sufficient radial strength so that it is capable of withstanding the structural loads, namely radial compressive forces imposed on the stent as it supports the walls of a vessel at the expanded target diameter. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Stents made from biostable or non-erodible materials, such as metals, have become the standard of care for percutaneous coronary intervention (PCI) as well as in peripheral applications, such as the superficial femoral artery (SFA). Such stents have been shown to be capable of preventing early and later recoil and restenosis. These permanent stents include bare metal stents and drug eluting stents which include a metallic base or scaffold with a polymer and drug coating.

In order not to affect healing of a diseased blood vessel, the presence of the stent is necessary only for a limited period of time. There are certain disadvantages to the presence of a permanent implant in a vessel such as compliance mismatch between the stent and vessel and risk of embolic events such as late stint thrombosis. To alleviate such disadvantages, a stent can be made from materials that erode or disintegrate through exposure to conditions within the body. Thus, erodible portions of the stent can disappear from the implant region after the treatment is completed, leaving a healed vessel. Stents fabricated from biodegradable, bioabsorbable, bioresorbable, and/or bioerodable materials such as bioabsorbable polymers can be designed to completely erode only after the clinical need for them has ended.

Polymers tend to have a lower strength on a per unit weight or volume basis than metals. As a result, the thickness of structural members or struts of a polymer scaffold tends to larger that metal stents. For example, a polymer scaffold for coronary applications may have a thickness, width, or both greater than 100 microns, greater than 120 microns, 100-200 microns, 120-180, 130-170, or 140-160 microns. Metallic stent struts may have a thickness, width, or both less than 100 microns, less than 80 microns, or 60 to 80 microns.

When a scaffold or stent is implanted, the struts of the stent project into the blood vessel. Since the struts project into the flow path of blood, the struts can create a resistance to and disrupt blood flow. Cumulative evidence, derived from intravascular ultrasound-based studies, has demonstrated a strong association between local endothelial shear stress (ESS) patterns and neointimal formation in bare metal stents, whereas in drug eluting stents there is contradictory data about the effect of ESS on vessel wall healing process. The effect of ESS on neointimal development following a bioresorbable scaffold implantation has remained unclear.

SUMMARY OF THE INVENTION

Embodiments of the invention include a method of treating vascular disease in a patient comprising: deploying a bioabsorbable polymer scaffold composed of a plurality of struts at a section or segment of an artery of a patient, the polymer scaffold expanding during deployment which expands the segment to a target diameter such that struts of the scaffold are apposed on a wall of the segment, wherein immediately upon deployment the struts disrupt flow of blood through the segment resulting in recirculation zones upstream and downstream of the struts that are in gaps between struts, wherein the recirculation zones are exposed to a low shear stress from the blood flow less than 1 Pa for at least 60% of a surface of the struts and luminal surfaces of the struts are exposed to a higher shear stress of at least 2 Pa, and wherein at least one year after deployment neointimal formation is higher in the recirculation zones than on the luminal surfaces of the struts. In these embodiments, at least one year after deployment a mean of the neointimal thickness is between 100 and 115 µm and a percentage volume obstruction of the a lumen of the segment by the scaffold is less than 10%.

Embodiments of the invention include a method of treating vascular disease in a patient comprising: expanding a bioabsorbable polymer in a segment of an artery of a patient such that the scaffold is expanded against a wall of the segment, wherein the scaffold comprises a coating including a polymer and a drug and the drug elutes from the coating into the artery, wherein flow of blood past the scaffold through the segment results in regions of low shear stress and regions of high shear stress immediately after the expanding, wherein after at least 80% of the drug elutes from the coating the regions of low shear stress promote neointimal proliferation resulting in a negative or inverse correlation between shear stress immediately after the expanding and the neointimal proliferation at least one year after the expanding.

Embodiments of the present invention include a method of treating vascular disease in a patient comprising: deploying a bioabsorbable polymer scaffold composed of a plurality of struts at a segment of an artery of a patient, the polymer scaffold expanding during deployment which expands the segment to a target diameter such that some of the struts of the scaffold are in contact with a wall of the segment, wherein immediately after deployment at least some of the struts are malapposed such that an abluminal surface of the malapposed struts is not in contact with the wall of the segment, wherein immediately upon deployment the malapposed struts disrupt flow of blood through the segment resulting in recirculation zones upstream and downstream of the struts that are in gaps between the malapposed struts, wherein the recirculation zones are exposed to a low shear stress from the blood flow less than 1 Pa for at least 60% of a surface of the malapposed struts, and wherein at least one year after deployment neointimal formation is higher in the recirculation zones than on the luminal surfaces of the struts.

The hemodynamic micro-environment appears to regulate neointimal response following a bioresorbable scaffold (e.g., an Absorb BVS) implantation. These findings underline the role of the ESS patterns on vessel wall healing and may be taken into consideration in the design of bioresorbable devices.

Several studies in the past have investigated the association between local ESS patterns and neointimal formation in bare metal and drug eluting stents. However, no study up to date has evaluated the effect of ESS on neointimal development following a bioresorbable scaffold implantation. The present application discloses an analysis which investigates the impact of the local hemodynamic environment on neointimal formation following a bioresorbable vascular scaffold. The analysis is based on studies of the Absorb BVS implantation in human patients.

The studies are based on twelve patients with an obstructive lesion in a relatively straight arterial segment who were treated with an Absorb BVS and had serial optical coherence tomographic examination at baseline and 1 year follow-up were included in the current analysis. The optical coherence tomographic data acquired at follow-up were used to reconstruct the scaffolded segment. Blood flow simulation was performed on the luminal surface at baseline defined by the Absorb BVS struts and the estimated ESS was related to the neointima thickness measured at 1 year follow-up.

At baseline the scaffolded segments were exposed to a predominantly low ESS environment (61% of the measured ESS was <1 Pa). At follow-up, the mean neointima thickness was 113±45 µm while the percentage scaffold volume obstruction was 13.1±6.6%. A statistical significant inverse correlation was noted between baseline logarithmic transformed ESS and neointima thickness at 1 year follow-up in all studied segments (average: −0.451, correlation coefficient range: −0.140 to −0.662). Mixed linear regression analysis between baseline ESS and neointima thickness at follow-up yielded a slope of −31 µm/log(Pa) and a y-intercept of 99 µm.

A statistically significant inverse association was found between ESS and NT in all the studied segments. These findings underscore the role of the local hemodynamic milieu on neointimal response and should be taken into consideration in the design of bioresorbable devices.

Embodiments of the invention include a method of treating vascular disease in a patient comprising: deploying a bioabsorbable polymer scaffold composed of a plurality of struts at a segment of an artery of a patient, the polymer scaffold expanding during deployment which expands the segment to a target diameter such that at least some of the struts of the scaffold are apposed on a wall of the segment, wherein the bioabsorbable polymer scaffold comprises an antiproliferative agent that elutes from the scaffold upon deployment, wherein immediately upon deployment the struts disrupt flow of blood through the segment resulting in recirculation zones upstream and downstream of the struts, wherein the recirculation zones are in gaps between the struts, wherein the recirculation zones are exposed to a low shear stress from the blood flow less than 1 Pa and luminal surfaces of the struts are exposed to a higher shear stress of at least 2 Pa, and wherein between deployment and one year after deployment neointimal formation is higher in the recirculation zones than on the luminal surfaces of the struts.

Embodiments of the any of the methods further include at least one year after deployment a mean of the neointimal thickness is between 100 and 115 µm and a percentage volume obstruction of the lumen of the segment is less than 10%; the low shear stress regions comprise recirculation zones between struts and the high shear stress regions comprise luminal surfaces of struts; the recirculation zones are between struts that are embedded at least 50% in the wall; the recirculation zones are between struts protruding at least 50% from the wall; the recirculation zones are between struts not in contact with the wall; the thickness (T)/width (W) is greater than 1.2; the thickness (T)/width (W) is less than 0.8.

Embodiments of the invention include methods of treating vascular disease in a patient comprising: expanding a bioabsorbable polymer scaffold composed of a plurality of struts in a stenotic segment of an artery of a patient such that the scaffold is expanded against a wall of the segment, wherein the scaffold comprises a coating including a polymer and an antiproliferative drug and the drug elutes from the coating into the artery after the expanding, wherein flow of blood past the scaffold through the segment results in regions of low shear stress and regions of high shear stress immediately after the expanding, wherein after at least 80% of the drug elutes from the coating the regions of low shear stress promote neointimal proliferation resulting in a negative or inverse correlation between shear stress immediately after the expanding and the neointimal proliferation at least one year after the expanding.

Embodiments of the invention include methods of treating a patient in need of treatment of coronary heart disease having a stenotic segment of a coronary artery comprising: selecting a bioabsorbable scaffold; identifying a negative or inverse correlation or association between neointimal proliferation and regions of low endothelial shear stress and high endothelial shear stress of an endothelial shear stress pattern or distribution at a segment or at a luminal surface the segment when the bioresorbable scaffold is deployed at the segment; and creating the endothelial shear stress pattern having the regions of low shear stress and high shear stress in the segment when the bioresorbable scaffold is deployed. The pattern or distribution may be immediately after deployment. The inverse correlation develops as the neointimal layer over and in between struts.

Embodiments of the invention include methods of treating a patient in need of treatment of coronary heart disease having a stenotic segment of a coronary artery comprising: selecting a bioabsorbable scaffold that elutes an antiproliferative agent when deployed; identifying a negative or inverse correlation or association between neointimal proliferation and regions of low endothelial shear stress and high endothelial shear stress of an endothelial shear stress pattern or distribution of the bioresorbable scaffold when deployed at the segment; and creating a blood flow disturbance along the segment with regions of high endothelial stress and regions of low endothelial shear stress when the bioresorbable scaffold is deployed at the segment; administering the antiproliferative agent to the segment from the bioresorbable scaffold, wherein the neointimal proliferation develops less than 1 year after deployment of the scaffold having a negative or inverse correlation between endothelial shear stress at deployment and neointimal thickness that develops after deployment; and the endothelial shear stress distribution affects neointimal formation such that there is increased neointima tissue in the regions between the struts and minimal neointima over the struts such as on the luminal surface of the struts such that the neointimal thickness between the struts is greater than the neointimal thickness over the luminal surface.

Embodiments of the invention include methods of treating a patient in need of treatment of coronary heart disease having a stenotic segment of a coronary artery comprising: determining characteristics of a bioabsorbable scaffold that provides a negative or inverse correlation between neointimal proliferation and regions of low endothelial shear stress and high endothelial shear stress of endothelial shear stress patterns at the segment when the bioresorbable scaffold is deployed at the segment; selecting a bioabsorbable scaffold based on the characteristics; creating the endothelial shear stress pattern having the regions of low shear stress and high shear stress in the segment when the bioresorbable scaffold is deployed. Embodiments of any of the methods may further include the characteristics are selected from the group in any combination consisting of drug delivery properties, strut thickness, strut width, ratio of strut thickness to strut width and the drug delivery properties comprise type of drug, dose of drug, coating polymer. The development of the negative or inverse correlation may be between deployment and 3 months after deployment, between 3 and 6 months after deployment, between 6 and 9 months after deployment, or between 9 months and 1 year after deployment. The development of the negative or inverse correlation may be between 0 and 3 months, between 3 and 6 months, or between 6 and 9 months after complete elution of antiproliferative agent from the scaffold.

In any of the disclosed methods, the scaffold flow disruption and drug delivery may provide for the formation of a protective thin layer of neointimal tissue without restricting the luminal dimensions, covers the underlying plaque and the scaffold struts which minimizes the risk for late scaffold thrombosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

INCORPORATION BY REFERENCE

Figure 1A:
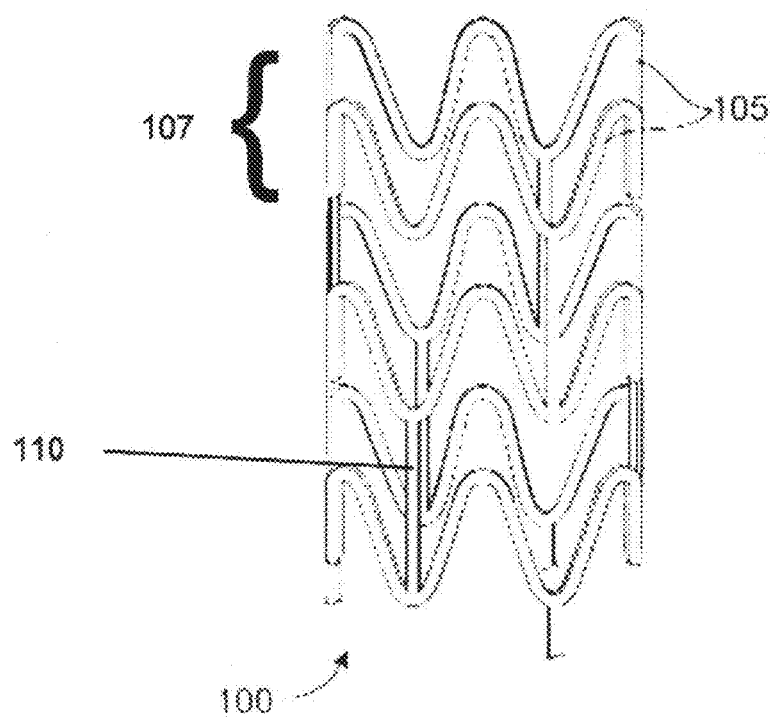
FIG. 1A depicts an exemplary stent scaffold.

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF THE INVENTION

Embodiments of the present invention include treatment of coronary artery disease and peripheral artery disease with bioresorbable polymer stents. The bioresorbable stents can include a support structure in the form of a scaffold made of a material that is bioresorbable, for example, a bioresorbable polymer such as a lactide-based polymer. The scaffold may be made partially or completely of a bioresorbable polymer. The scaffold may include non-polymer and/or nonbiodegradable parts or additives. The scaffold is designed to completely erode away from an implant site after treatment of an artery is completed. The scaffold can further include a drug, such as an antiproliferative or anti-inflammatory agents. A polymer coating disposed over the scaffold can include the drug which is released from the coating after implantation of the stent. The polymer of the coating is also bioresorbable.

The treatment methods can apply to bioresorbable scaffolds for both coronary and peripheral treatment. Bioresorbable polymer scaffolds for coronary artery treatment can have a length between 12 to 18 mm. Such coronary scaffolds may be laser cut from polymer tubes with a diameter between 2.5 mm to 4.5 mm and with a thickness/width of 100-200 microns, or more narrowly, 140-160 microns. A bioresorbable polymer scaffold for peripheral treatment, for example, SFA treatment is typically longer, a larger diameter, and may have thicker struts than a coronary scaffold. For example, the scaffolds may have a length 18 and 36 mm, 36 and 40 mm or even between 40 and 200 mm. An SFA scaffold may be cut from tubing with a diameter of between 5-10 mm, 6-8 mm and a wall thickness of about greater than 150 microns, for example, 150 to 250 microns, 250 to 300 microns, 300 to 350 microns, 350 to 400 microns, or greater than 400 microns.

The coronary scaffold may be configured for being deployed by a non-compliant or semi-compliant balloon from about a 1.1 to 1.5 mm diameter (e.g., 1.35 mm) crimped profile. Exemplary balloon sizes include 2.5 mm, 3.0 mm, 3.5 mm, and 4.0 mm, where the balloon size refers to a nominal inflated diameter of the balloon. The scaffold may be deployed to a diameter of between 2.5 mm and 5 mm, 2.5 to 4.5 mm, or any value between and including the endpoints. The pressure of the balloon to deploy the scaffold may be 12 to 20 psi. Embodiments of the invention include the scaffold in a crimped diameter over and in contact with a deflated catheter balloon.

The intended deployment diameter may correspond to, but is not limited to, the nominal deployment diameter of a catheter balloon which is configured to expand the scaffold. The balloon pressure and the diameter to which the balloon inflates and expands the scaffold may vary from deployment to deployment. For example, the balloon may expand the scaffold in a range between the nominal inflated diameter to the nominal inflated diameter plus 0.5 mm, e.g., a 3.0 mm balloon may expand a scaffold between 3 and 3.5 mm. In any case, the inflated diameter at deployment is less than the rated burst diameter of the balloon.

A scaffold may be laser cut from a tube (i.e., a pre-cut tube) that is less than or greater than an intended deployment diameter. For example, a pre-cut tube diameter may be 0.7 to 1 times or 1 to 1.5 times the intended deployment diameter or any value in between and including the endpoints.

The scaffolds and coating of the present invention may be made of or include bioresorbable polymer including poly (L-lactide) (PLLA), poly(D-lactide) (PDLA), polyglycolide (PGA), poly(D,L-lactide (PDLLA), and poly(L-lactide-co-glycolide) (PLGA). The PLGA include those having a mole % of (LA:GA) of 85:15 (or a range of 82:18 to 88:12), 95:5 (or a range of 93:7 to 97:3), or commercially available PLGA products identified being 85:15 or 95:5 PLGA. Additional bioresorbable polymers include but are not limited to polyhydroxyalkanoates (PHA), poly(4-hydroxybutyrate) (P4HB), poly(ε-caprolactone), (PCL) poly(trimethylene carbonate) (PTMC), poly(butylene succinate) (PBS), poly(p-dioxanone) (PDO), poly(ester amides) (PEA), and including copolymers (block, random, alternating) and blends of any combination of polymers disclosed.

The present invention is applicable to, but is not limited to, self-expandable stents, balloon-expandable stents, stent-grafts, and generally tubular medical devices in the treatment of artery disease. The present invention is further applicable to various stent designs including wire structures, and woven mesh structures.

Self expandable or self expanding stents include a bioabsorbable polymer scaffold that elastically expands to the target diameter upon removal of an external constraint. The self expanding scaffold expands to a larger diameter when an external constraint is removed. This external constraint could be applied with a sheath that is oriented over a compressed scaffold. The sheath is applied to the scaffold after the scaffold has been compressed by a crimping process. After the stent is positioned at the implant site, the sheath may be retracted by a mechanism that is available at the end of the catheter system and is operable by the physician. The self expanding bioabsorbable scaffold property is achieved by imposing only elastic deformation to the scaffold during the manufacturing step that compresses the scaffold into the sheath.

The bioabsorbable scaffold may also be expanded by a balloon. In this embodiment the scaffold is plastically deformed during the manufacturing process to tightly compress the scaffold onto a balloon on a catheter system. The scaffold is deployed at the treatment site by inflation of the balloon which expands the scaffold. The balloon will induce areas of plastic stress in the bioabsorbable material to cause the scaffold to achieve and maintain the appropriate diameter on deployment.

A stent scaffold can include a plurality of cylindrical rings connected or coupled with linking elements. For example, the rings may have an undulating sinusoidal structure. When deployed in a section of a vessel the cylindrical rings are load bearing and support the vessel wall at an expanded diameter or a diameter range due to cyclical forces in the vessel. Upon deployment, the scaffold may recoil inward slightly, for example less than 5% or 10%. Load bearing refers to the supporting of the load imposed by radial inwardly directed forces. Structural elements, such as the linking elements or struts, are generally non-load bearing, serving to maintain connectivity between the rings. For example, a stent may include a scaffold composed of a pattern or network of interconnecting structural elements or struts.

FIG. 1A depicts a view of an exemplary stent 100. In some embodiments, a stent may include a body, backbone, or scaffold having a pattern or network of interconnecting structural elements 105. Stent 100 may be formed from a tube (not shown). FIG. 1A illustrates features that are typical to many stent patterns including undulating sinusoidal cylindrical rings 107 connected by linking elements 110. As mentioned above, the cylindrical rings are load bearing in that they provide radially directed force to support the walls of a vessel. The linking elements generally function to hold the cylindrical rings together. A structure such as stent 100 having a plurality of structural elements may be referred to as a stent scaffold or scaffold. Although the scaffold may further include a coating, it is the scaffold structure that is the load bearing structure that is responsible for supporting lumen walls once the scaffold is expanded in a lumen.

The structural pattern in FIG. 1A is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1A, can be formed on a tube or sheet with a technique such as laser cutting or chemical etching. The stent can then be crimped on to a balloon or catheter for delivery into a bodily lumen. Exemplary scaffolds are disclosed in U.S. Patent Publication No. 2008-0275537.

Methods of treating coronary heart disease may include identifying a segment of a blood vessel that is stenotic in a patient in need of treatment of coronary heart disease (CAD) and expanding the segment to a reference vessel diameter through implantation of a bioresorbable scaffold at the segment. The method may further include releasing drug from the scaffold for up to 2 to 3 months after the expanding to control neointimal proliferation to reduce narrowing of the segment due to smooth cells that proliferate and form a neointima layer at a surface of a wall of the segment. The scaffold may provide support to the segment at an expanded diameter for less than 6 months after deployment. A compliance of the supported segment is dominated by a compliance of the scaffold which is less than a natural compliance of a blood vessel. The vessel wall of the segment may be remodeled during the supporting so that an increased diameter is maintained after the supporting when a radial strength of the scaffold decreases due to biodegradation of the scaffold. The increased diameter allows for increased blood flow compared to the stenotic segment. An endothelial or neointimal layer is formed that incorporates or covers the scaffold within 4 to 6 months of implantation of the scaffold. The compliance of the remodeled segment may be restored to the natural compliance of a blood vessel through the decrease in the radial strength of the scaffold, loss of connectivity between struts of the scaffold, and erosion of the scaffold from the segment. Vasomotion may be restored to the remodeled segment as the compliance is restored that of a healthy blood vessel.

The stenotic segment, for example, may be a single denovo stenotic lesion with a diameter stenosis that is 50% or more. Restoring vasomotion may correspond to vasodilation of at least 3% of a mean luminal diameter of the remodeled segment. The segment may be supported for 1 to 4 months after the increasing. Some treatments may include increasing of at least one of mean lumen area, minimal lumen area, and lumen volume between the 6 months and 2 years after deployment as the radial strength decreases, as the connectivity between struts of the scaffold is lost, and as the scaffold erodes from the segment. Further details of treatment may be found in US 2010/019833.

The ABSORB Bioresorbable everolimus eluting vascular scaffold (ABSORB BVS) of Abbott Vascular Inc. of Santa Clara, Calif. was recently developed to provide an approach to treating coronary artery lesions with transient vessel support and drug delivery. Preclinical evaluation in an animal model demonstrated substantial polymer degradation at 2-years post ABSORB BVS implantation, with complete disappearance of the BVS strut "footprint" in the vessel wall within a 3-4 year period. The first generation BVS (BVS revision 1.0) was tested in the ABSORB cohort A trial and demonstrated promising results with a low event clinical rate at up to 4 years follow up (EuroIntervention 2012; 7:1060-1061). The device was however limited by a slightly higher acute recoil compared to conventional metallic platform stents.

Improvements in design were therefore introduced in the second generation BVS (BVS revision 1.1), notably an enhanced mechanical strength, more durable support to the vessel wall, a reduced maximum circular unsupported surface area and a more uniform strut distribution and drug delivery. The performance of the next generation BVS revision 1.1 was subsequently investigated in the ABSORB Cohort B Trial which reported excellent clinical results at 1 and 2 year follow-up (J Am Coll Cardiol. 2011; 58: B66).

Figures 1B, 1C:
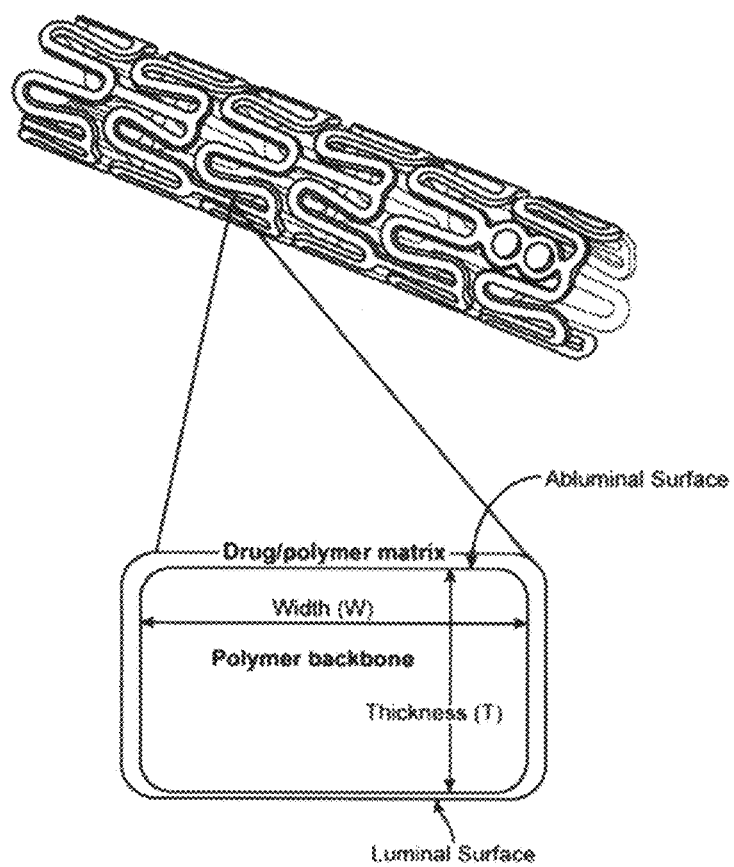
FIGS. 1B-C depict an exemplary scaffold.

FIGS. 1B-C depicts the BVS revision 1.1 scaffold. FIG. 1B shows the scaffold in a crimped configuration. FIG. 1C show a cross-section of a strut showing the polymer backbone or core of the strut surrounded by a drug/polymer matrix. The cross-section of the strut has an abluminal surface or side that faces the vessel wall and a luminal surface or side that faces the lumen of the vessel. The strut cross-section shown is rectangular with rounded corners with a width (W) and thickness T. The BVS revision 1.1 scaffold is approximately square with an aspect ratio T/W close to 1.

The polymer backbone is made of poly(L-lactide). The diameter of the scaffold in an as-fabricated or pre-crimped configuration is 3 mm and the length is 18 mm. The struts may have a width of about 165 microns and thickness of about 152 microns, for example, 156 microns. The coating is a mixture of poly(DL-lactide) and everolimus with a 1:1 ratio of polymer to drug. The coating is about 2 to 2.5 microns in thickness.

In general, the treatment with bioabsorbable polymer stents has a number of advantages over permanent implants: (i) The stent disappears from the treated site resulting in reduction or elimination of late stent thrombosis; (ii) disappearance of the stent facilitates repeat treatments (surgical or percutaneous) to the same site; (iii) disappearance of the stent allows restoration of vasomotion at the treatment site (the presence of a rigid permanent metal stent restricts vasomotion); (iv) the bioabsorbability results in freedom from side-branch obstruction by struts; (v) the disappearance results in freedom from strut fracture and ensuing restenosis. Some of these advantages may be relevant to improving clinical outcomes for diabetic patients.

In the short term and over the long term, a bioresorbable scaffold has the advantage of being less traumatic to the vessel wall. Since the bioresorbable scaffold degrades with time and eventually disappears, trauma associated with the presence of a scaffold decreases with time and eventually disappears.

Neointimal formation is modulated by several factors including the vessel wall trauma caused during stent deployment, the plaque burden, the composition of the underlying plaque, as well as local endothelial shear stress (ESS) patterns (e.g., Hoffmann, et al., J Am Coll Cardiol 1998; 31:43-9). Several clinical and experimental studies have provided evidence that local hemodynamic factors, in particular low ESS, promote neointimal formation in bare metal stents whereas in drug eluting stents the association between ESS and neointimal proliferation is weak and appears to be affected by the mechanisms of action and probably the release kinetics of the eluted drug (e.g., Papafaklis, JACC Cardiovasc Interv 2010; 3:1181-9).

Bioresorbable scaffold is a new technology introduced to overcome the long term implications of metallic caging as these devices have the unique ability to disappear after implantation, allowing restoration of vessel physiology (Serruys, Eur Heart J 2012; 33:16-25b). The first clinical studies provided evidence about the safety and efficacy of these devices and revealed a gradual increase of the neointima tissue which, however, was accommodated by the expanding scaffold and did not appear to affect luminal dimensions (Ormiston et al., Circ Cardiovasc Interv 2012; 5:620-32). It has been demonstrated that neointima tissue has an asymmetric distribution around the circumference of the vessel wall indicating that local factors (i.e., vessel wall trauma, increased plaque inflammation and local hemodynamics) are likely to be involved and regulate this process (Brugaletta et al., 2012; 221:106-12).

The aim of the present invention and the associated analysis is the impact of ESS on neointima proliferation following a bioresorbable vascular scaffold implantation. In contrast to previous reports optical coherence tomographic (OCT) data it utilized to reconstruct the surface of the scaffolded segment at baseline, simulate blood flow and assess vessel wall healing. "Baseline" refers to the time point immediately after the stent is deployed in the vessel, and if the stint is balloon expandable, after the balloon is removed from the implant site. The high resolution of this imaging technique allows more detailed reconstruction of luminal morphology and evaluation of the hemodynamic micro-environment following device implantation and its impact on neointimal growth.

Data was analyzed from patients recruited in the second group of the ABSORB Cohort B Trial (A Clinical Evaluation of the Everolimus Eluting Bioresorbable Vascular Scaffold System in the Treatment of Patients with de Novo Native Coronary Artery Lesions) (NCT00856856). The study design has already been described in detail by Serruys et al. Circulation 2010; 122:2301-12. In brief, 101 patients with single or two vessel de novo coronary disease implanted with an Absorb BVS (Abbott Vascular, Santa Clara, Calif., USA) (dimensions: 3.0×18 mm) were included in this prospective multicenter trial. The studied population was divided in two groups. Both groups had serial angiographic, grayscale intravascular ultrasound (IVUS), IVUS virtual histology and OCT evaluation at three time points. The first group (B1) had these tests at baseline post device implantation, 6 months and 2 years follow-up, while the second group (B2) had these investigations at baseline, 1 year and 3 years follow-up. The current analysis included only the patients from Cohort B2 who had received an Absorb BVS in a relatively straight coronary segment and had undergone OCT evaluation at baseline and 1 year follow-up.

Coronary reconstruction was performed using only the OCT data neglecting the vessel curvature. To minimize the error introduced by this approximation relatively straight arterial segments were analyzed. The angulation of the treated segments was assessed using a previously described methodology (Gomez-Lara et al., JACC Cardiovasc Interv 2010; 3:1190-8). In brief, in an angiographic view with minimal foreshortening and overlapping we measured the angulation of the treated segment—extended from the nearest proximal to the implanted lesion side branch to the nearest distal side branch—by estimating the angle defined by the tangents of the centerlines of the 5 mm proximal and distal portions of the analyzed segment. The cutoff value used to categorize straight and curved segments in the current analysis was the mean+2 standard deviations (29 degrees) of the angulations measured during balloon inflation in all the segments treated in the Absorb Cohort B study (Gomez-Lara et al.).

OCT image acquisition was performed at baseline (immediately after scaffold implantation) and at 1 year follow-up using a C7XR Fourier Domain system (Lightlab Imaging, Westford, Mass., USA). The data acquired at baseline were analyzed by two expert observers—blinded to patients' procedural and clinical characteristics—who reviewed the scaffolded segment and identified in each frame the embedded, the protruded, and the malapposed struts. Embedded struts were struts of which their surface was greater than 50% impacted into the vessel wall. Struts were considered protruded when they were in contact with the vessel wall but with less than 50% of their surface being impacted into the vessel wall. Struts were considered malapposed when the struts were such that their abluminal surface was not in contact with the vessel wall. The feasibility of this classification has already been tested and the reported results have shown a high inter-observer agreement (K index: 0.75) (Gomez-Lara et al., JACC Cardiovasc Interv 2011; 4:992-1001).

The existence of and the degree of embedding, protrusion, and malapposition can depend on the shape and degree of narrowing of the vessel wall at the implant site. The existence of and the degree of embedding, protrusion, and malapposition can also depend on the deployment diameter and balloon pressure. For example, the scaffold may be deployed at some value greater than the nominal inflated diameter of the balloon.

Incomplete apposition can occur at intervention (deployment) and persist for several months. Additionally, stent struts can dislodge from complete apposition with the vessel wall after intervention and is referred to as late-acquired stent apposition (LAISA). U.S. Patent Application No. 2010/0198331. For example, the struts may dislodge 1, 2, 3, 4 months after intervention or 1 to 5, 1 to 2, 2 to 3, 3 to 4, or 4 to 5 months after intervention. In either case, the struts can disrupt blood flow and cause high and low shear stress regions as described. It is expected that the negative or inverse correlation between ESS and neointimal proliferation will occur for both types of dislodged struts.

The regions between struts can be between any combination of embedded, protruding, or malapposed struts. It is expected that the ESS will vary between the different combinations and result in different degrees of neointimal proliferation in the regions and on top of the struts.

Figure 2:
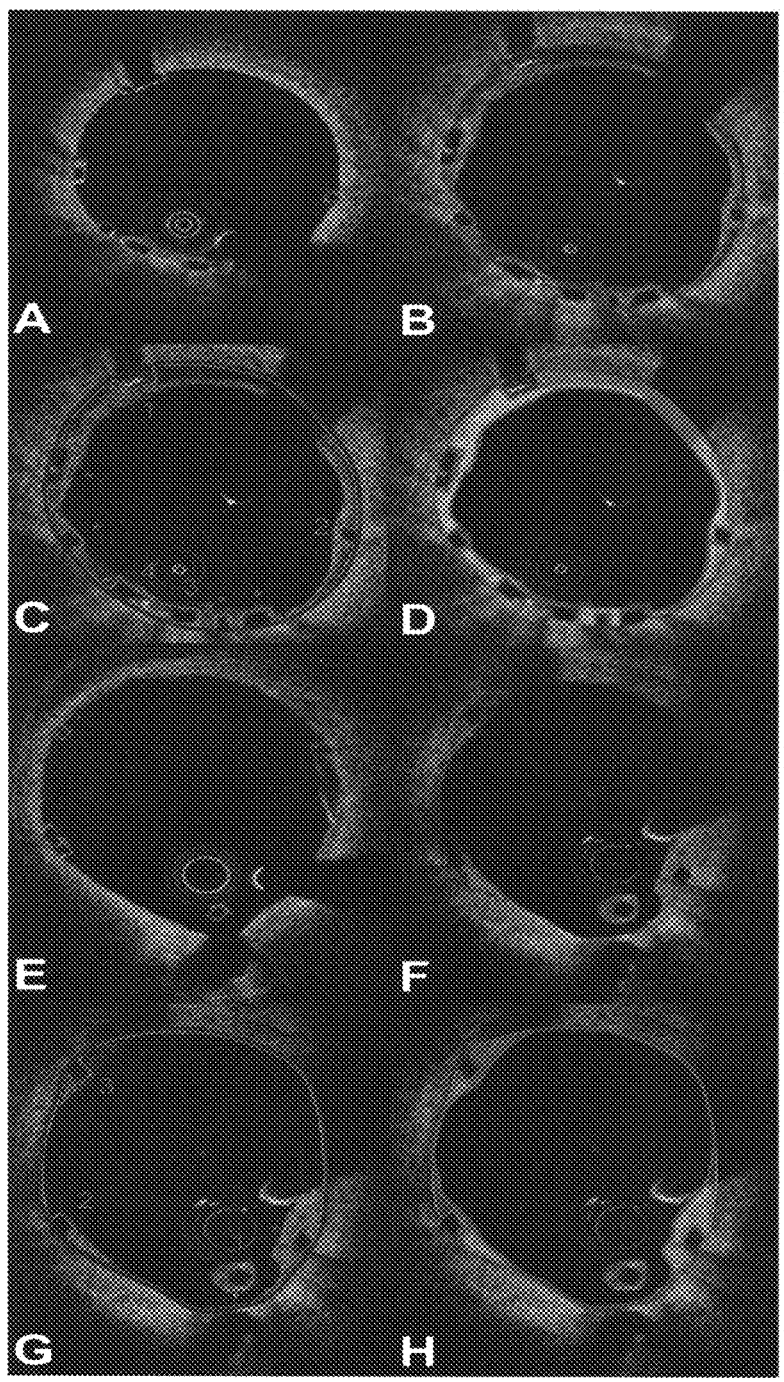
FIG. 2 depicts optical coherence tomographic image acquired at baseline (A) and the corresponding frame obtained at 1 year follow-up showing the distal end of a scaffolded segment (the distal marker is located at 11 o'clock) (B).

FIG. 2 depicts optical coherence tomographic image acquired at baseline (A) and the corresponding frame obtained at 1 year follow-up showing the distal end of a scaffolded segment (the distal marker is located at 11 o'clock) (B). The green line in panel C corresponds to the luminal border at baseline as defined in the follow-up frame, whereas the blue line defines the scaffold perimeter, the gravitational center of which was used for the correct placement of the detected borders on the vessel backbone. The two observers were able to identify four corresponding struts in the baseline and follow-up frames two of which (strut 3 and 4) were embedded at baseline. It was not possible to identify correspondence for four struts (indicated with an asterisk) at the frame acquired at follow-up. The area between the luminal border at baseline (green line) and the luminal border at follow-up up (red line) corresponds to the neointima tissue that is portrayed in Panel D in a semi-transparent fashion. In a second case example strut malapposition (strut 1) was noted in two corresponding OCT images acquired at baseline (E) and 1 year follow-up (F). In this location the baseline and follow-up luminal border as well as the scaffold perimeter is defined by the endoluminal side of the neointima (G, H).

The data acquired at 1 year follow-up were used to reconstruct two surfaces: 1) the luminal surface at baseline post scaffold implantation and 2) the luminal surface at 1 year follow-up. In each follow-up OCT examination the observers identified the frames portraying, the scaffolded segment and analyzed 1 frame at every 0.4 mm interval in the non-scaffolded segment and 1 frame at 0.2 mm interval in the scaffolded segment. The luminal morphology at baseline was approximated by the luminal borders in the non-scaffolded segment at 1 year follow-up. In the scaffolded segment the observers identified corresponding struts between baseline and follow-up OCT examinations and in case that the baseline struts were embedded the baseline luminal borders were defined by splines connecting the adluminal sides of the struts (portrayed at the frames acquired at 1 year follow-up), whereas in case that the baseline struts were protruded or malapposed the baseline luminal borders was defined by the adluminal sides of the struts (portrayed at the frames acquired at 1 year follow-up) and between struts by the segment connecting the abluminal sides of adjacent struts (FIG. 2). For the struts that were not possible to identify correspondence between baseline and follow-up examinations, we assumed that these struts were protruded since the majority of the struts were protruded at the baseline examination (Gomez-Lara et al., JACC Cardiovasc Interv 2011; 4:992-1001).

The luminal surface at follow-up was constructed by the luminal borders in the scaffolded segment defined by the endoluminal borders of the neointima. Malapposed struts at 1 year follow-up were not taken into consideration and in these segments' the baseline luminal border was approximated by the endoluminal border of the neointima (FIG. 2). Segments exhibiting extensive malapposition (malapposition seen in >25' of the scaffolded segment) were excluded from the analysis.

Figure 3:
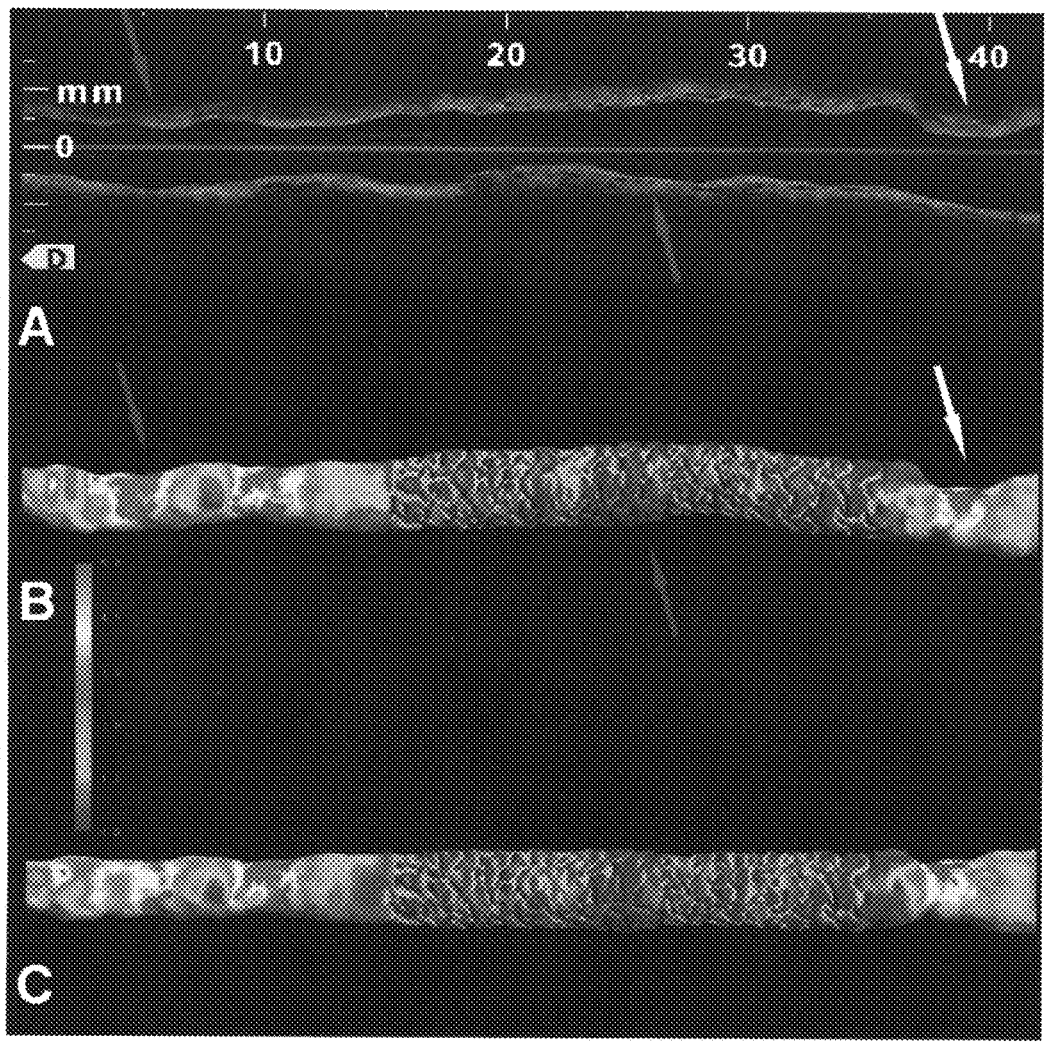
FIG. 3 depicts a longitudinal optical coherence tomographic (OCT) view of a coronary segment implanted with an Absorb bioresorbable scaffold (A).

FIG. 3 depicts longitudinal optical coherence tomographic (OCT) view of a coronary segment implanted with an Absorb bioresorbable scaffold (A). An eccentric calcified plaque (white, left-most arrow) noted at the proximal edge of the scaffold. The arrows indicate changes in the position of the OCT catheter with regards the lumen wall (initially the OCT catheter was closer to the upper border, then to the low border and finally to the upper border). These changes are due to the three dimensional (3D) geometry of the vessel, the vessel motion during the cardiac circle and plaque protrusion into the lumen. Panel B shows the reconstructed artery with the endothelial shear stress (ESS) portrayed in the 3D surface with the use of a-color coded map (low ESS corresponds to the blue and high to the red color). In contrast to the model showed in Panel B the model portrayed in Panel C was obtained after positioning the detected borders on the vessel backbone using the gravitational center of the luminal borders in the non-scaffolded segment and the scaffold in the scaffolded segment. It is apparent that the change in the vessel geometry has an impact on the ESS distribution especially in segments with eccentric-protruded plaques (white arrow) and increased curvature. Although this approach is likely to distort the real geometry of the model when eccentric plaques are present it is expected to give more accurate reconstruction in the scaffolded segment where the scaffold is anticipated to be symmetrically expanded and have a round-shaped morphology.

The vessel centerline was approximated by a straight segment with a length equal to the length of the studied coronary and divided into equidistant sub-segments corresponding to the number of the OCT frames. To minimize the error introduced by the lateral displacement of the OCT catheter in the coronary artery during pull-back (caused by the lateral movements of the coronary artery during the cardiac circle) the gravitational centers of the luminal borders in native segments were estimated, and of the scaffold (defined by the abluminal side of the scaffold) in scaffolded segments, and used them for placing the detected borders onto the vessel centerline. In particular each border was placed perpendicularly onto the corresponding sub-segment in such a way so that the relevant gravitational center is located in the middle of the sub-segment (FIG. 3). This approach is likely to distort the anatomy of eccentric lesions located proximally or distally to the scaffold but, on the other hand, it is expected to provide a more accurate representation of the coronary morphology in the scaffolded segment and eliminate the wave-like artifacts introduced by the movement of the catheter (during the cardiac circle) which can affect the ESS measurements (FIG. 3).

The final outcome of this process is two non-uniform rational B-spline surfaces: the first representing the luminal surface at baseline (constructed by the luminal borders in the non-scaffolded segment and by the scaffold borders in the scaffolded segment) and the second represented the luminal surface at 1 year follow-up (constructed by the luminal borders in the scaffolded segment).

The obtained geometries were further processed with computational fluid dynamics techniques for the generation of a finite volume mesh. Anisotropic meshes with unstructured tetrahedral elements were generated for each baseline surface using an automated mesh generation program (ICEM CFD, Ansys, Canonsburg, Pa.). To capture the detailed characteristics of the hemodynamic micro-environment, mesh density was increased around the stent struts and within the boundary layer of the flow field, and had a maximum element edge equal to approximately ¼ of the BVS strut thickness (i.e., ~40 μm). Blood flow simulation was performed by solving the 3D Navier-Stokes equations (CFX 11, Ansys). Blood was considered as a homogeneous, Newtonian fluid with a dynamic viscosity of 0.0035 Pa·s and a density of 1,050 kg/m$^3$. Blood flow was modeled to be laminar and incompressible with a steady flow profile at the inlet of the reconstructed segment. Coronary blood flow for each artery was estimated by measuring in two angiographic projections—obtained at baseline, post scaffold implantation the number of frames required for the contrast agent to pass from the inlet to the outlet of the reconstructed segment, the volume of the segment at baseline and the cine frame rate. The arterial wall was considered to be rigid and no-slip conditions were applied at the baseline luminal surface, while zero pressure conditions were imposed at the outlet. ESS at baseline luminal surface was calculated as the product of blood viscosity and the gradient of blood velocity at the wall.

In the scaffolded segment, the lumen volume at baseline and 1 year follow-up was estimated and the neointimal volume was defined as: lumen volume at baseline−lumen volume at follow-up whereas the percentage volume obstruction as: 100×neointima volume/lumen volume at baseline. Neointimal thickness (NT) was calculated as the distance between the luminal surface at baseline and the luminal surface at follow-up using an in-house developed algorithm implemented in Visual Fortran (Compaq Computer Corporation, Houston, Tex.) (Papafaklis et al., Int J Cardiol 2009; 134:25-32). Positive values corresponded to areas of neointimal hyperplasia. NT was measured along the axial direction per 0.2 mm and around the vessel circumference per 5° for each cross section and was associated to ESS at the corresponding location. Segments within the scaffold located at the origin of side branches and their adjacent segments with length equal to the diameter of the side branch were excluded from the analysis since the branches were not included in the 3D reconstruction, and thus ESS assessment in these areas is not considered to be reliable.

Continuous variables are presented as mean±standard deviation whereas categorical as counts and percentages. Pearson correlation coefficient and linear regression analysis were implemented to investigate the association between the logarithmic transformed ESS and the estimated NT at follow-up. To control patient effect, a mixed model with random intercept and slope was used to estimate the overall association between the logarithmic transformed ESS and NT. In this mixed model, the autoregressive covariance structure was utilized to take into consideration of the nested structure of cross-sections within subjects.

The interobserver agreement in the identification of corresponding struts between baseline and follow-up examination was evaluated with the use of the Cohen's kappa test. A P value<0.05 was considered statistical significant. Statistical analysis was performed with the SPSS statistical software package (version 18.0 for Windows, SPSS, Inc, Chicago, Ill.).

Twenty one patients (22 lesions) from Cohort B2 were investigated with OCT at baseline and 1 year follow-up. In 14 patients (14 arteries) the treated segments had angulation<29°. Two cases were excluded from the analysis: the first because of extensive malapposition and the second because of poor OCT image quality. Thus 12 segments were reconstructed. The baseline characteristics of the studied population are shown in Table 1. Most of the patients suffered from hypercholesterolemia (58%) and had hypertension (67%) and 83% were treated for stable angina.

TABLE 1

Baseline characteristics of the studied population.

| | Studied Population (n = 12) |
|---|---|
| Baseline characteristics | |
| Age (years) | 61 ± 9 |
| Male | 8 (67%) |
| Hypertension | 8 (67%) |
| Hypercholesterolemia | 7 (58%) |
| Diabetes mellitus | 0% (0) |
| Current smoking | 4 (33%) |
| Prior percutaneous coronary intervention | 1 (8%) |
| Prior myocardial infarction | 2 (17%) |
| Stable angina | 10 (83%) |
| Unstable angina | 1 (8%) |
| Silent ischemia | 0 (0%) |
| Treated vessel | |
| Left anterior descending artery | 9 (75%) |
| Left circumflex artery | 2 (17%) |
| Right coronary artery | 1 (8%) |
| Ramus intermedious | 0 (0) |
| Medications | |
| β-blockers | |
| Renin-angiotensin aldosterone inhibitors | |
| Statins | |

The length of the reconstructed segments was 47.6±10.5 mm whereas the length of the scaffolded segment was 19.6±0.8 mm. Neointimal proliferation was evident in all treated segments that resulted in a percentage scaffold volume obstruction of 13.1±6.6% (Table 2). The mean NT derived from the measurements in the 12 patients (patient level analysis) was 113±45 μm (range: 72-200 μm).

In general, the mean neointima thickness may be between 90 and 120 μm, 100 and 115 μm, or 100 and 110 μm while the percentage scaffold volume obstruction may be less than 5%, less than 10%, less than 15%, or less than 20%. The mean neointima thickness may be between 90 and 120 μm, 100 and 115 μm, 100 and 110 μm, 110 and 115 μm while the percentage scaffold volume obstruction may be less than 5%, less than 10%, less than 15%, less than 20%, 5 to 10%, 10 to 15%, 15 to 20%, or 5 to 20% for any of the scaffolds disclosed herein. Any combination of scaffolds disclosed, mean intimal thickness, and volume obstruction is disclosed.

TABLE 2

Quantitative analysis of the scaffolded segment in the 3 dimensional reconstructed arteries.

| | Studied Population (n = 12) |
|---|---|
| Baseline mean lumen area (mm²) | 6.70 ± 1.35 |
| Follow-up mean lumen area (mm²) | 5.85 ± 1.43 |
| Mean neointima tissue area (mm²) | 0.85 ± 0.38 |
| Mean neointima thickness (μm) | 113 ± 45 |
| Lumen volume at baseline (mm³) | 130.9 ± 25.7 |
| Lumen volume at follow-up (mm³) | 114.6 ± 28.2 |
| Neointima tissue volume (mm³) | 16.4 ± 6.9 |
| Percentage volume obstruction (%) | 13.1 ± 6.6 |

Methods of treatment of a patient having coronary heart disease include identifying a bioabsorbable polymer scaffold composed of a plurality of struts for deploying at a stenotic segment of an artery of the patient, such that the scaffold expands the segment to a target diameter such that at least some of the struts of the scaffold are apposed on a wall of the segment. The method may include identifying blood flow regions past the struts that have higher neointimal formation and regions that have lower neointimal formation at follow-up-times post-deployment. The method further includes identifying blood flow regions past the struts that have lower shear stress and blood flow regions that have higher shear stress at the time of deployment. The method further includes associating the regions of higher neointimal formation with the lower shear stress regions and the regions of lower neointimal formation with the high shear stress regions. The scaffold is then provided for deployment in the patient followed by deployment in the patient.

The lower shear stress regions may be identified as recirculation zones upstream and downstream of the struts that correspond to gaps between the struts wherein immediately upon deployment the struts disrupt flow of blood through the segment. The higher shear stress regions may be identified as the luminal surfaces of the struts. The recirculation zones may be exposed to a low shear stress from the blood flow less than 1 Pa and luminal surfaces of the struts may be exposed to a higher shear stress which may be greater than 1 Pa or 2 Pa. The follow-up time may be identified as at least 3 months, 6; months, 1 year, 3 to 6 months, or 6 months to 1 year. The struts corresponding to the regions may be identified as malapposed struts.

Figure 4:
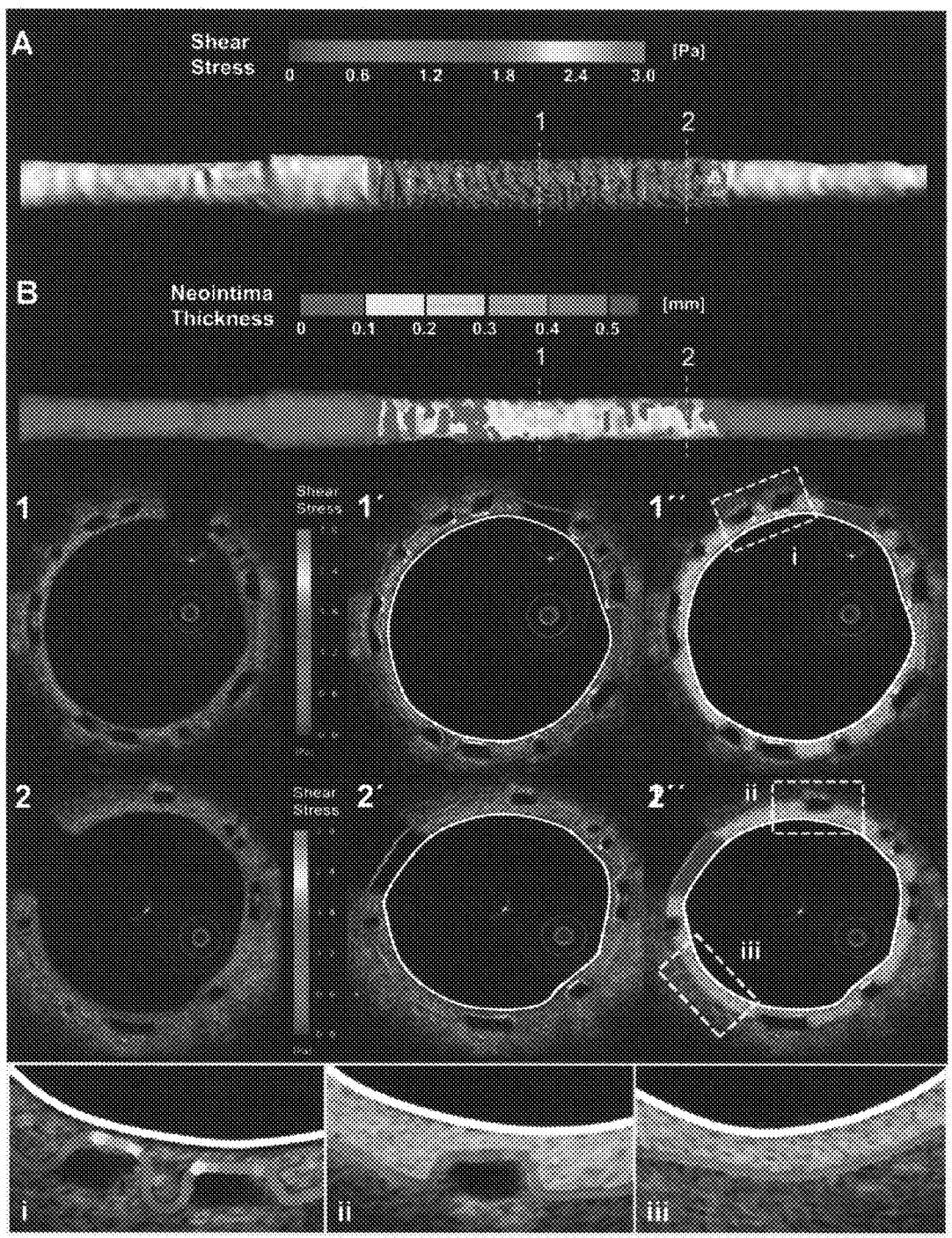
FIG. 4 depicts a three dimensional reconstruction of baseline luminal surface at the scaffolded segment.

FIG. 4 depicts a three dimensional reconstruction of baseline luminal surface at the scaffolded segment. Panel (A) illustrates the endothelial shear stress (ESS) distribution in the scaffolded segment portrayed in a color-coded map (with the red color indicating high shear stress and the blue low shear stress) and (B) the corresponding neointima thickness. The dash lines in panel A and B indicate the location of the optical coherence tomographic images 1 and 2 in the reconstructed segment. Panel 1' and 2' show the ESS distribution at baseline across the circumference of the vessel wall and panel 1" and 2" the neointima thickness portrayed in a semi transparent fashion. As it is shown in panels i, ii, iii the ESS is low in the between the struts areas and high on the top of the struts. The neointima tissue appears increased in segments with low ESS and reduced in segments with high ESS values.

Figure 5:
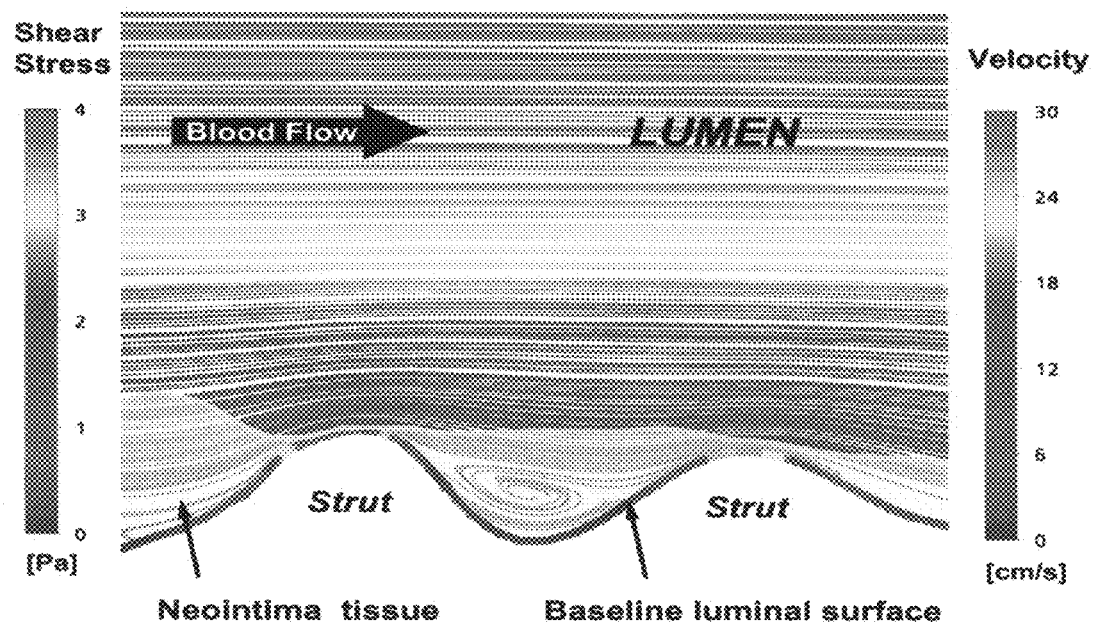
FIG. 5 depicts a longitudinal section of a scaffolded section demonstrating the blood flow streamlines with velocity color coding.

FIG. 5 depicts a longitudinal section of a scaffolded section demonstrating the blood flow streamlines with velocity color coding. The endothelial shear stress (ESS) distribution along the baseline luminal surface is portrayed in a color coded map, whereas the neointima thickness at 1 year follow-up is shown in a semitransparent fashion. Low velocities and ESS, as well as recirculation zones are noted in the inter-strut areas or regions, whereas ESS values are high on the top of the struts, i.e., on or around the luminal surface of the struts. The ESS distribution appears to affect neointimal formation, as there is increased neointima tissue in the regions between the struts and minimal neointima over the struts, particularly the luminal surface of the struts.

In general, the ESS values at the top of a strut, i.e., the luminal surface, for a bioresorbable scaffold may be greater than 1 Pa, 1.2 Pa, 1.5 Pa, or 2 Pa. The ESS values may be 1 to 2 Pa, 1.2 to 2 Pa, or 1.2 to 2 Pa.

In the 12 patients (patient level analysis) the mean ESS measured in the scaffolded segments at baseline was 1.10±0.35 Pa. Cross sectional level analysis showed that 61% of the computed ESS were <1 Pa. As it is shown in FIG. 4 the protruded struts created a rough luminal surface at baseline that affected the local hemodynamic micro-environment. Flow recirculation zones were noted proximally and distally to the protruded struts resulting in low ESS in these regions and relatively high ESS on the top of the struts (FIG. 5). The low ESS noted in these areas appeared to have affected neointima formation with an increased tissue formation proximally and distally to the scaffold struts and limited neointima formation on the top of the struts (FIGS. 4 and 5).

A negative correlation coefficient (average: −0.451; statistically different from 0) was noted between ESS at baseline and logarithmic transformed NT at 1 year follow-up in all patients (P<0.001). Table 3 provides the correlation coefficients between the logarithmic transformed baseline ESS and the NT for each subject, as, well as the estimated slopes and y-intercepts after applying linear regression analysis for each subject (FIG. 5). The linear mixed-effect model yielded an overall slope of −31 μm/log(Pa) and y-intercept of 99 μm.

Figure 6A:
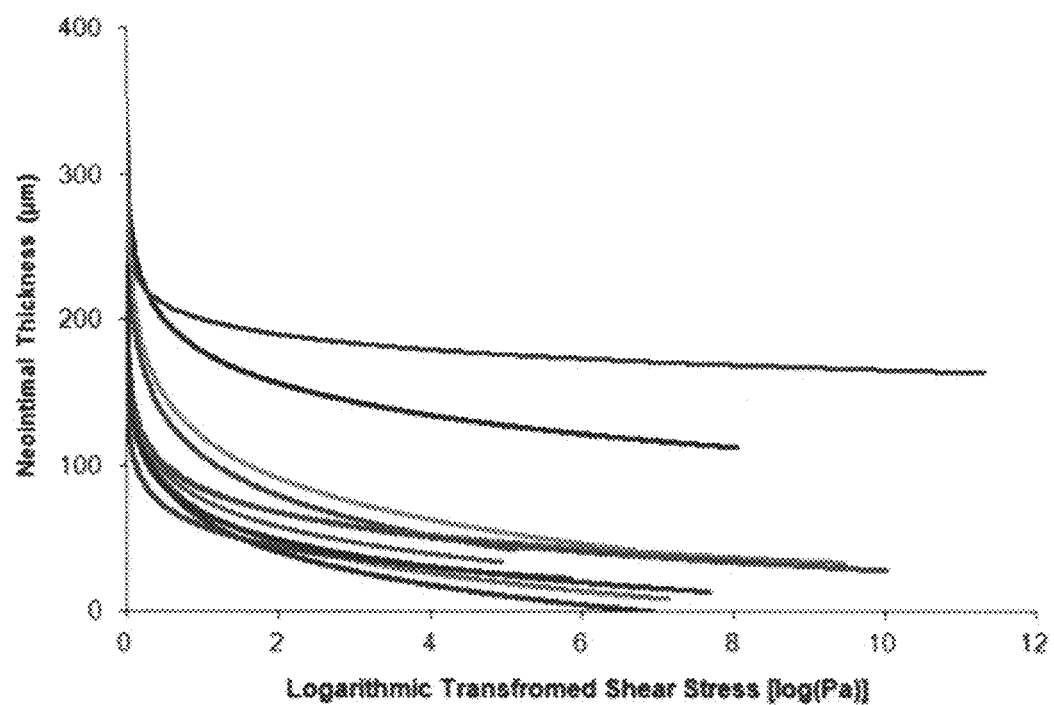
FIG. 6A depicts regression curves showing the association between the logarithmic transformed ESS at baseline and neointima thickness at follow-up in the 12 segments included in the current analysis.
Figure 6B:
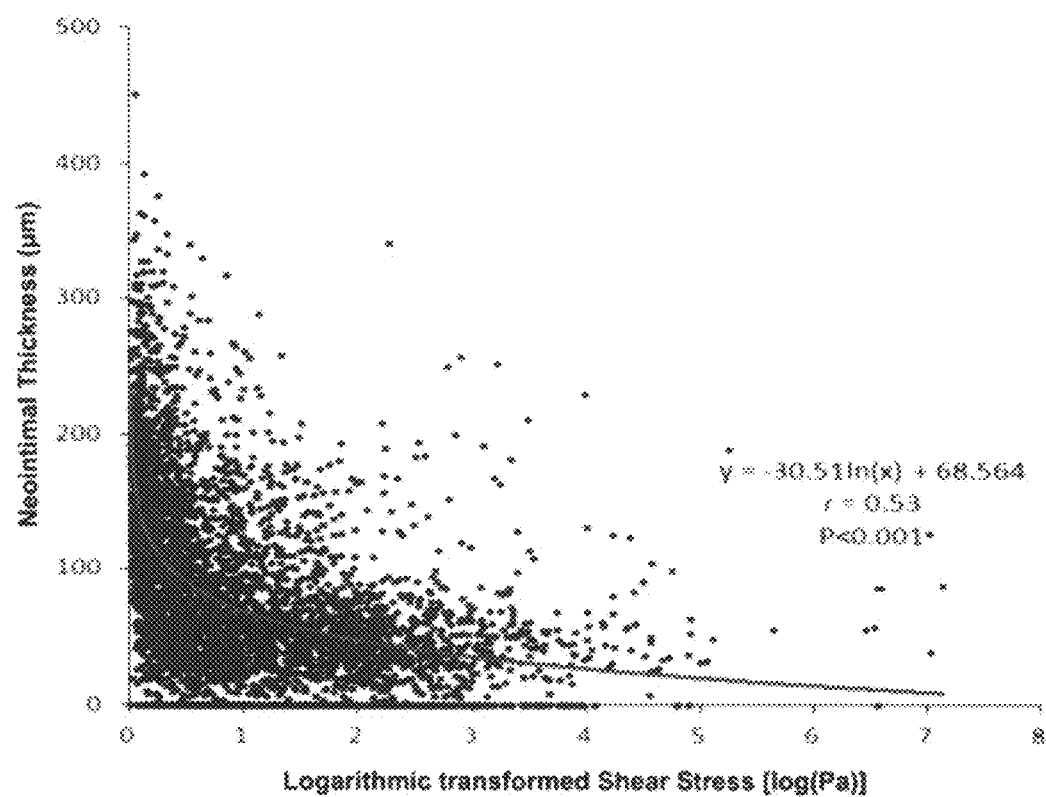
FIG. 6B depicts linear regression analysis between the logarithmic transformed ESS and neointima thickness for a typical patient case.

FIG. 6A depicts regression curves showing the association between the logarithmic transformed ESS at baseline and neointima thickness at follow-up in the 12 segments included in the current analysis. FIG. 6B depicts linear regression analysis between the logarithmic transformed ESS and neointima thickness for a typical patient case.

TABLE 3

Correlation coefficient, slope and y-intercept obtained after applying linear regression analysis between logarithmic transformed baseline ESS and neointimal thickness at 1 year follow-up in each patient case.

| Patient number | Correlation coefficient | Slope (μm/(log)Pa) | y-intercept (μm) |
|---|---|---|---|
| 1 | −0.480 | −30 | 116 |
| 2 | −0.412 | −37 | 181 |
| 3 | −0.140 | −35 | 206 |
| 4 | −0.426 | −26 | 57 |
| 5 | −0.386 | −28 | 84 |
| 6 | −0.488 | −29 | 85 |
| 7 | −0.533 | −31 | 69 |
| 8 | −0.590 | −34 | 65 |
| 9 | −0.662 | −39 | 122 |
| 10 | −0.410 | −24 | 58 |
| 11 | −0.428 | −33 | 72 |
| 12 | −0.455 | −30 | 68 |

The reliability of the two observers in identifying corresponding struts between baseline and the follow-up examinations was examined in 100 frames randomly selected from 8 patients. The Kappa index was 0.79 indicating a good agreement.

In the presently described study serial OCT data, for the first time, and computational fluid dynamics techniques were used to evaluate the effect of the hemodynamic microenvironment on neointimal formation post implantation for a bioresorbable scaffold (Absorb BVS). It was found that 1) the thick protruded struts (strut thickness: 156 μm) of the implanted scaffold create a rough surface which causes flow disturbance and recirculation zones resulting in low ESS and 2) that the reported low ESS contributed to neointimal formation as there was a negative correlation in all the studied segments between ESS and NT.

Several computational experimental and clinical reports in the past have examined the effect of stent implantation on local hemodynamics and the association between ESS and neointimal formation. In silico blood flow simulation studies have underscored the effect of stent design on local hemodynamic patterns with the stents having thick rectangular-shaped struts to cause flow disruption and lead to a low ESS environment, whereas the devices with thin circular-shaped struts appear to minimally influence the local flow and ESS (e.g., Duraiswamy et al., 2009; 131:061006). Clinical studies in 3D models obtained from patient data have shown an inverse correlation between ESS and NT in bare metal stents, whereas in drug eluting stents there are conflicting reports (e.g, Gijsen et al., Am J Cardiol 2003; 92:1325-8). Gijsen et al demonstrated an inverse relation between ESS and neointimal formation in patients treated with sirolimus eluting stents, whereas Suzuki et al found that ESS had no impact on neointimal development in diabetic patients implanted with the same type of stent. Papafaklis et al evaluated the association between neointimal formation and ESS in 10 patients implanted with paclitaxel eluting stents and 10 patients treated with sirolimus eluting stents, and found an inverse correlation between ESS and NT in the paclitaxel arm, but no significant association in the group of patients implanted with sirolimus eluting stents, advocating that these findings are due to the different pathophysiological effect of each drug on vessel wall healing and the pro-restenotic ESS biological pathway (Papafaklis, JACC Cardiovasc Interv 2010; 3:1181-9). However, a significant limitation of the abovementioned studies is the fact that neointimal formation was measured assuming that stent struts were well apposed post device implantation and that coronary reconstruction was based on IVUS, an imaging modality with a limited radial resolution which cannot accurately evaluate the lumen surface irregularities caused by the stent struts and the modest neointima proliferation in drug eluting stents.

The study disclosed herein overcame the abovementioned pitfalls as it uses for the first time OCT to reconstruct the coronary lumen. OCT with its high radial resolution allows reliable evaluation of luminal morphology, detailed assessment of strut apposition, and accurate estimation of NT. In addition, the heterogeneity of appearance of the struts of the Absorb BVS in OCT permits identification of the correspondence between baseline and follow-up examinations and use this information for more reliable reconstruction of the baseline luminal surface (Gutierrez-Chico et al., Circ J 2012; 76:342-50). The high resolution of OCT allowed confirmation for the first time in vivo the findings of computational flow dynamic studies on theoretical models and demonstrate that the thick protruded struts disrupt flow resulting in recirculation zones in front and especially behind the struts. These regions are exposed to low ESS (ESS was <1 Pa in 61% of surface of the studied segments) which appears to promote vessel wall healing (Stone, et al., Circulation 2011; 124:763-5).

In contrast to previous reports which showed that rapamycin-analogues abrogate the effect of ESS on neointimal formation, a statistically significant correlation was found between ESS and NT in all studied segments implanted with an everolimus eluted BVS (e.g., Papafaklis, JACC Cardiovasc Interv 2010; 3:1181-9). This discrepancy should be attributed to the more reliable evaluation of NT thickness and baseline ESS patterns in the segments reconstructed by OCT data as well as to the longer follow-up period. In previous studies the association between NT and ESS was evaluated at 6 and 9 months follow-up; only 3 or 6 months after the complete elution of the antiproliferative drug (Yazdani et al., 2011; 7:835-43). In Absorb BVS 80% of the everolimus elution is released within the first month after device implantation. It can be speculated that after the first month the low ESS promoted neointimal formation resulting in a negative association between ESS at baseline and neointimal formation at 1 year follow-up (Ormiston et al., Lancet 2008; 371:899-907). The negative association between ESS and NT may result in treatment with bioabsorbable stents with different scaffold materials, coating materials, and drugs.

The analysis described herein is focused on the association between ESS and NT at 1 year follow-up and not at other time points (i.e. at 3 years follow-up or at 6 months or 2 years follow-up using the data of ABSORB Cohort B1 group) for the following reasons: 1) half of the baseline OCT examinations in the Cohort B1 group were performed by an M-3 Time Domain system which has different radial and axial resolution and image quality from the C7XR Fourier Domain system and thus it is not feasible to find corresponding struts between baseline and follow-up examinations, 2) our objective was not to compare our findings with the results of the IVUS based reconstruction studies in metallic drug eluting stents but to examine the midterm effect of ESS on NT where the antiproliferative drug has been eluted and the effect of vessel wall injury has been dissipated and 3) although it would be interesting to compare the association between ESS and NT at 2 different follow-up time points (i.e. at 1 year follow-up and 3-year follow-up)—as it has been shown that neointimal tissue continues to develop—the proposed analysis cannot be applied at 2-year or 3-year follow-up since the scaffold loses its structural integrity after 1 year and expands; thus we cannot approximate the baseline luminal surface in the scaffolded segment based on the location of the struts at 2 or 3 years follow-up (e.g., Ormiston et al., Circ Cardiovasc Interv 2012; 5:620-32).

This appears to be the first study which examines the effect of ESS on neointimal proliferation post bioresorbable scaffold implantation. It was found that the depolymerization of the scaffold's struts does not impede the mechano-transduction pathways that regulate the response of the free vessel wall to the local hemodynamic micro-environment (e.g., Oberhauser et al., EuroIntervention 2009; 5 Suppl F:F15-22). Hence, the current configuration (strut thickness: 156 μm) and composition (poly-L-lactide struts, covered by a thin layer of an amorphous matrix of poly-D,L-lactide that controls the release of the antiproliferative drug—everolimus) of the Absorb BVS provides a template for the formation of a potentially protective thin layer of neointimal tissue which without restricting the luminal dimensions, covers the underlying plaque and the scaffold's struts, minimizing the risk for late scaffold thrombosis.

The observations regarding the relationship between ESS and neointimal proliferation may also apply to other bioabsorbable stents made from other scaffold materials, coating polymers, and drugs. Scaffold and coating polymers can include, polylactide-based (PLA-based) polymers such as poly(D,L-lactide), poly(D,L-lactide) 96/4, poly(L-lactide-co-D,L-lactide), poly(L-lactide-co-glycolide), poly(D,L-lactide-co-glycolide), poly(L-lactide-co-caprolactone), poly(D, L-lactide-co-caprolactone), and poly(D, L-lactide) made from polymerization of a racemic mixture of L- and D-lactides. The caprolactone copolymers may have 1 to 5 mol % or wt % caprolactone units. A scaffold or coating polymer may be a blend or copolymer of PLLA, PLGA, and PCL. The coating polymer may also be a blend of any combination of the above polymers. The coating polymer may also be a blend of a PLA based polymer and polycaprolactone with 1 to 5 mol % or wt % of polycaprolactone. Any combination of the above polymers can be used for scaffold and coating polymers.

Scaffold materials may also include bioerodible metals and metal alloys, for example, magnesium, magnesium alloys, iron, and iron alloys. The bioerodible metallic scaffold may further include a drug delivery coating including any of the coating polymers disclosed.

The stent or scaffold may also have no drug delivery coating. The stent or scaffold may have a drug coating of a neat drug, i.e., with no polymer. The stent or scaffold may also have drug dispersed within the scaffold with or without a drug-delivery coating.

The drug delivery coating of any of the stents disclosed can include one or more drugs. Exemplary drugs include, but are not limited to, rapamycin, structural derivatives and functional analogues of rapamycin, biolimus, everolimus, merilimus, myolimus, novolimus, paclitaxel, 16-pent-2-ynyloxy-32(S)-dihydro-rapamycin, ridaforolimus, sirolimus, tacrolimus, temsirolimus, clobetasol, and zotarolimus. Embodiments may include any combination of drug, scaffold material, and coating polymer. An exemplary embodiment may include a scaffold made of a polylactide-based polymer and a coating including the same or different polylactide-based polymer and Novolimus.

The ratio of drug to polymer in a drug delivery coating may be 1:5 to 5:1, 1:2 to 2:1, or 1:1. The drug dose per mm of stent length may be 3 to 4 micrograms (mcg), 4 to 5 mcg, 5 to 6 mcg, 6 to 8 mcg, 3 mcg, 4 mcg, 5 mcg, or 6 mcg.

The strut thickness of the polymer or metallic scaffolds, with or without a drug delivery coating, can be 80 to 200 microns, 80 to 100 microns, 100 to 120 microns, 120 to 140 microns, 140 to 160 microns, 160 to 180 microns, 180 to 200 microns, 150 to 200 microns, 170 microns, 165 microns, 125 microns, 150 microns, or 160 microns.

Exemplary bioabsorbable stents are in Table 4.

TABLE 4

Exemplary bioabsorbable stents

| Example | Scaffold Polymer | Coating Polymer | Drug | Strut thickness (microns) |
|---|---|---|---|---|
| 1 | PLLA | PLA-based, PDLLA, PLLA | Sirolimus | 100, 100 to 110, 120, or 120 to 130 |
| 2 | PLLA | None | None | 100, 100 to 110, 120, or 120 to 130 |
| 3 | PLLA | None | None | 170 |
| 4 | Mg alloy | None | None | 155 |
| 5 | Mg alloy | PLA-based, PLLA, or PLGA | Paclitaxel | 125 |
| 6 | Mg Alloy | PLA-based, PLLA, or PLGA | Sirolimus | 150 |
| 7 | PLA-based | PLA-based | Novolimus or Myolimus | 150, 100 to 140, 140 to 160 |
| 8 | PLA-based | PLA-based | Sirolimus | 150 to 170, 160 |

The molecular weight in terms of number average or weight average molecular weight of scaffold polymer may be 70 to 100 kDa, 90 to 100 kDa, 100 to 150 kDA, 150 to 200 kDa, 200 to 250 kDa, 250 to 300 kDa, 300 to 350 kDa, 350 to 400 kDa, 400 to 500 kDa, 500 to 750 kDa, 750 to 1000 kDa, 1000 to 1200 kDa, or greater than 1200 kDa. The intrinsic viscosity of the scaffold polymer in units of dL/g may be 2 to 2.5, 2.5 to 3, 3 to 3.5, 3.5 to 4 to 4.5, 4.5 to 5, 5 to 5.5, 5.5 to 6, 6 to 6.5, 6.5 to 7, 7 to 7.5, 7.5, 7.5 to 8, 8 to 8.5, and 8.5 to 9.

Referring to FIG. 1C, the strut cross-section can have a T/W greater than 1, for example, 1 to 1.2, 1.2 to 1.3, 1.3 to 1.5, 1.5 to 1.8, 1.8 to 2, 2 to 2.5, or greater than 1.2, 1.3, 1.5, 1.8, 2, or 2.5. In the case of T/W greater than 1, it is expected that the blood flow disruption and the ESS at the top of the strut would increase as T/W increases. Based on the negative or inverse correlation between ESS and neointimal proliferation, it is further expected the neointimal proliferation would decrease as the T/W increases. Alternatively, the strut cross-section can have a T/W less than 1, for example, 0.9 to 1, 0.7 to 0.9, or 0.5 to 0.7, or 0.5 to 0.7 or less than 0.9, 0.7, 0.5, 0.3, 0.2, or less than 0.2. It is expected that the blood flow disruption and ESS decreases at the top of the strut would decrease as T/W decreases. Based on the negative correlation between ESS and neointimal proliferation, it is further expected the neointimal proliferation would increase as the T/W decreases.

Therefore, the T/W can be adjusted to obtain a desired protective layer over the top of the strut without restricting the luminal dimensions and covering underlying plaque and the scaffold struts to minimize risk of late stent thrombosis.

The T/W can be adjusted so that at baseline the scaffolded segments were exposed to a predominantly low ESS environment, at least 60% of the measured ESS may be less than 2 Pa, less than 1 Pa, or less than 0.5 Pa and at follow-up, the mean neointima thickness may be between 90 and 120 μm, 100 and 115 μm, or 100 and 110 μm while the percentage scaffold volume obstruction may be less than 5%, less than 10%, less than 15%, less than 20%, between 5 and 10%, between 10 and 15%, between 15 and 20%, or between 10 and 20%.

Methods of treatment of patients in need of treatment of coronary heart disease can be based on or modified by any of the observations herein such as the negative or inverse correlation between ESS and NT resulting from deployment of a bioabsorbable scaffold. The steps can apply to any of the bioabsorbable scaffolds described herein. The methods of treatment can be based on or modified include one or more steps. The method of treatment can include identifying a bioabsorbable as providing a negative correlation between ESS and NT developing at a time within a year after deployment of the scaffold. The development of the negative correlation can be identified as present or developing between deployment and 3 months, between 3 and 6 months after deployment, between 6 and 9 months after deployment, or between 9 months and 1 year after deployment. The methods of treatment can include selecting the bioabsorbable scaffold based on the negative correlation between the ESS and NT. The methods of treatment can include selecting the bioabsorbable scaffold over another stent or scaffold based on the negative or inverse correlation between the ESS and NT.

Significant limitations of the current analysis are the assumptions that the reconstructed arteries were straight segments and that the scaffold was symmetrically expanded. To minimize the error introduced by the first approximation we included relatively straight coronary arteries, as of present, there is no method that has been demonstrated to reliably fuse frequency domain OCT and angiographic data for complete coronary representation. We have recently reported a high minimal luminal/maximal luminal diameter ratio (0.85±0.08) in IVUS cross sectional images of segments implanted with an Absorb BVS 1.1 fact that indicates a symmetric expansion of the device (Brugaletta, et al., Catheter Cardiovasc Interv 2012; 79:19-28). However, potential asymmetries in scaffold's expansion which may have affected the estimated association between ESS and NT cannot be excluded. The effect of malapposed struts on local hemodynanics was not taken into account in this analysis. Considering the overall low reported prevalence of malapposed struts and the fact that we excluded segments with extensive malapposition, it is unlikely for this approximation to have affected our results (Gomez-Lara et al., JACC Cardiovasc Interv 2011; 4:992-1001).

Serial OCT data to reconstruct the coronaries and evaluate the effect of the hemodynamic micro-environment on neointimal formation after Absorb BVS implantation. A statistically significant inverse association was found between ESS and NT in all the studied segments. These findings underscore the role of local hemodynamic milieu on vessel wall healing and should be taken into consideration in the design of bioresorbable devices.

What is claimed is:

1. A method of treating vascular disease in a patient comprising:
   deploying a bioabsorbable polymer scaffold composed of a plurality of struts at a segment of an artery of a patient,
   wherein each of the plurality of struts is made completely of a bioabsorbable polymer between a luminal surface and an abluminal surface of each of the struts, the polymer scaffold expanding during deployment which expands the segment to a target diameter,
   wherein at least some of the struts of the deployed scaffold are apposed struts such that their abluminal surfaces are in contact with a wall of the segment and at least some of the struts of the deployed scaffold are malapposed struts such that their abluminal surfaces are not in contact with the wall of the segment, wherein at least some of the apposed struts are impacted greater than 50% into the wall, wherein at least some of the apposed struts are impacted less than 50% into the wall, wherein the bioabsorbable polymer scaffold comprises a coating on a surface of the scaffold, the coating including a mixture of a coating polymer and a drug and the drug elutes from the coating into the artery upon deployment, wherein the struts have a thickness (T), a width (W), an aspect ratio (T/W) of 0.7 to 0.9, and a T of 80 to 100 microns, wherein immediately upon deployment the struts disrupt flow of blood through the segment resulting in recirculation zones upstream and downstream of the struts that are in gaps between struts, wherein the recirculation zones are exposed to a low shear stress from the blood flow less than 1 Pa for at least 60% of a surface of the struts and luminal surfaces of the struts are exposed to a higher shear stress of at least 2 Pa, and wherein at least one year after deployment neointimal formation is higher in the recirculation zones than on the luminal surfaces of the struts.

2. The method of claim 1, wherein at least one year after deployment a mean of the neointimal thickness is between 100 and 115 μm and a percentage volume obstruction of a lumen of the segment by the scaffold is less than 10%.

3. The method of claim 1, wherein the scaffold comprises a polymer including a blend of poly(L-lactide) and poly(L-lactide-co-caprolactone).

4. The method of claim 1, wherein the scaffold comprises a polymer comprising poly(L-lactide).

5. A method of treating vascular disease in a patient comprising:

deploying a bioabsorbable polymer scaffold composed of a plurality of struts at a segment of an artery of a patient, wherein each of the plurality of struts is made completely of a bioabsorbable polymer between a luminal surface and an abluminal surface of each of the struts, the polymer scaffold expanding during deployment which expands the segment to a target diameter, wherein at least some of the struts of the deployed scaffold are apposed struts such that their abluminal surfaces are in contact with a wall of the segment and at least some of the struts of the deployed scaffold are malapposed struts such that their abluminal surfaces are not in contact with the wall of the segment, wherein at least some of the apposed struts are impacted greater than 50% into the wall, wherein at least some of the apposed struts are impacted less than 50% into the wall, wherein the bioabsorbable polymer scaffold comprises a coating on a surface of the scaffold, the coating including a coating polymer and a drug and the drug elutes from the coating into the artery upon deployment, wherein the struts have a thickness (T), a width (W), and an aspect ratio (T/W) greater than 1.2, wherein immediately upon deployment the struts disrupt flow of blood through the segment resulting in recirculation zones upstream and downstream of the malapposed struts that are in gaps between the struts, wherein the recirculation zones are exposed to a low shear stress from the blood flow less than 1 Pa for at least 60% of a surface of the struts and luminal surfaces of the struts are exposed to a higher shear stress of at least 2 Pa, and wherein at least one year after deployment neointimal formation is higher in the recirculation zones than on the luminal surfaces of the struts.

6. The method of claim 1, wherein a protective layer of neointimal tissue over luminal surfaces of the struts is formed without restricting luminal dimensions of the segment and which covers underlying plaque and the struts to minimize risk of late stent thrombosis.

7. The method of claim 1, wherein the drug is novolimus.

* * * * *